(12) United States Patent
Fletcher et al.

(10) Patent No.: US 6,495,012 B1
(45) Date of Patent: Dec. 17, 2002

(54) SENSOR FOR ELECTROMETRIC MEASUREMENT

(75) Inventors: Kenneth S. Fletcher, Hartford, CT (US); David N. Skinner, Milton, MA (US); Ellen Candela, Cohasset, MA (US); Michael M. Bower, Wareham, MA (US)

(73) Assignee: The Foxboro Company, Foxboro, MA (US)

( * ) Notice: Subject to any disclaimer, the term of this patent is extended or adjusted under 35 U.S.C. 154(b) by 0 days.

(21) Appl. No.: 09/541,358

(22) Filed: Mar. 31, 2000

(51) Int. Cl.[7] .............................................. G01N 27/401
(52) U.S. Cl. ....................................... 204/435; 204/420
(58) Field of Search .................................. 204/420, 435

(56) References Cited

U.S. PATENT DOCUMENTS

| | | | |
|---|---|---|---|
| 3,103,480 A | * | 9/1963 | Watanabe et al. |
| 3,282,818 A | * | 11/1966 | Nolan |
| 3,410,779 A | * | 11/1968 | Whitehead et al. |
| 3,445,368 A | | 5/1969 | Detemple ................... 204/195 |
| 3,455,793 A | * | 7/1969 | Watanabe et al. |
| 3,528,903 A | | 9/1970 | Taylor ........................ 204/195 |
| 3,652,439 A | * | 3/1972 | Ben-Yaakov et al. |
| 4,002,547 A | | 1/1977 | Neti et al. ................... 204/195 |
| 4,162,211 A | | 7/1979 | Jerrold-Jones .............. 204/195 |
| 4,310,400 A | * | 1/1982 | Mark et al. |
| 4,333,812 A | * | 6/1982 | Bukamier et al. |
| 4,390,406 A | * | 6/1983 | Kato et al. |
| 4,447,309 A | * | 5/1984 | Morioka et al. |
| 4,681,115 A | * | 7/1987 | Holscher |
| 4,913,793 A | | 4/1990 | Leonard ...................... 204/433 |
| 5,139,641 A | | 8/1992 | Neuken ....................... 204/435 |

FOREIGN PATENT DOCUMENTS

DE     0 247 535 A     12/1987 .................... 27/30

OTHER PUBLICATIONS

"A Reference Electrode with Free–Diffusion Liquid Junction for Electrochemical Measurements under Changing Pressure Conditions", Analytical Chemistry, vol. 69, No. 13, Jul. 1, 1997.

* cited by examiner

*Primary Examiner*—T. Tung
(74) *Attorney, Agent, or Firm*—Kevin A. Oliver; W. Hugo Liepmann; Foley Hoag & Eliot LLP

(57) ABSTRACT

The invention provides a sensor with a reference electrode and a flowing electrolyte which is particularly useful for measuring the ion concentration of a process solution. The invention includes a sensor having a pressurized reservoir which provides flow of an electrolyte, a non-metallic solution ground and a resistance temperature device bonded to a non-metallic solution ground. The invention provides sensors with greater accuracy and stability by minimizing or eliminating ingress of contaminants from a process solution through the external junction of the sensor.

70 Claims, 4 Drawing Sheets

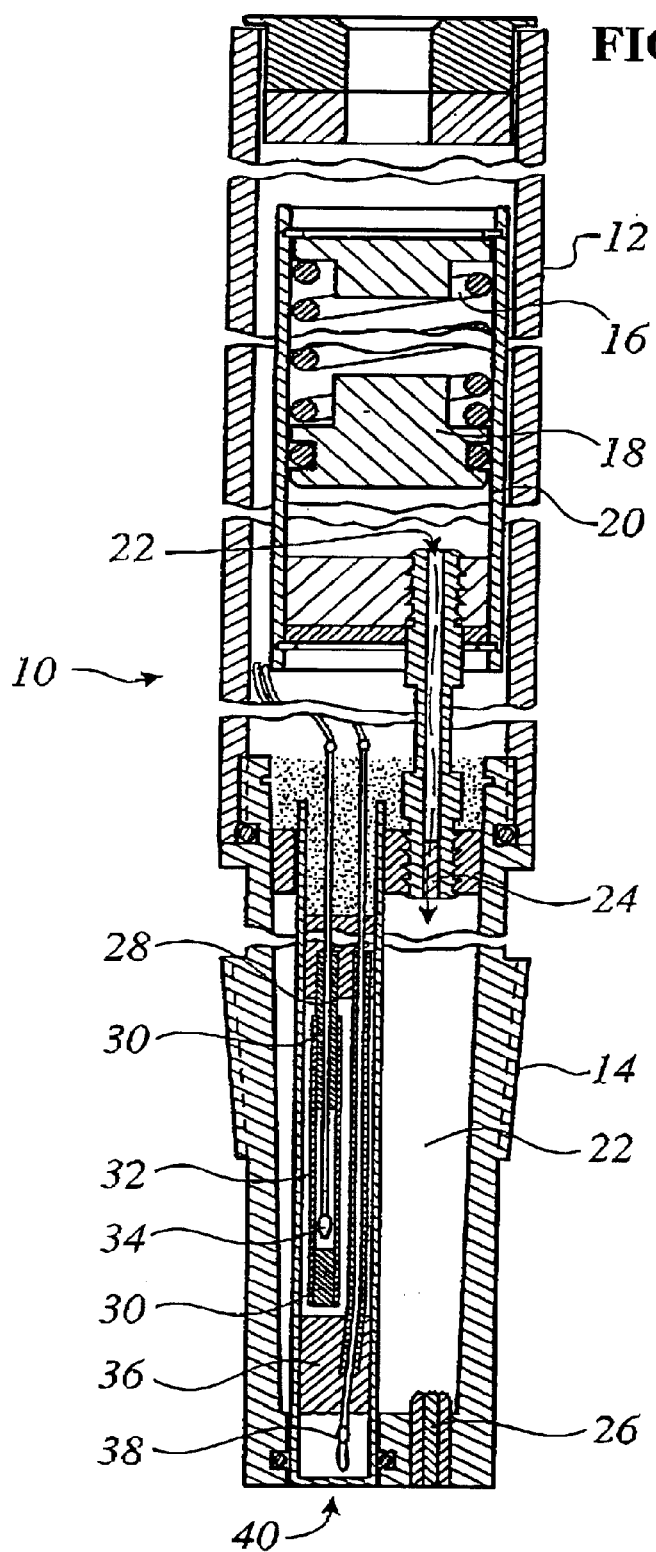
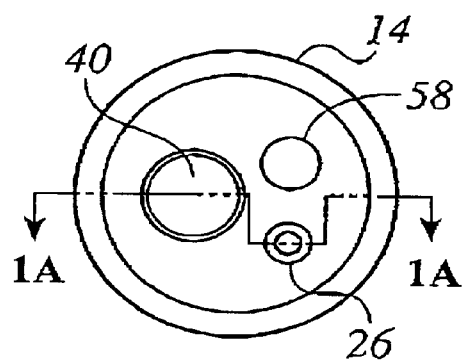
FIG. 1A
FIG. 1B

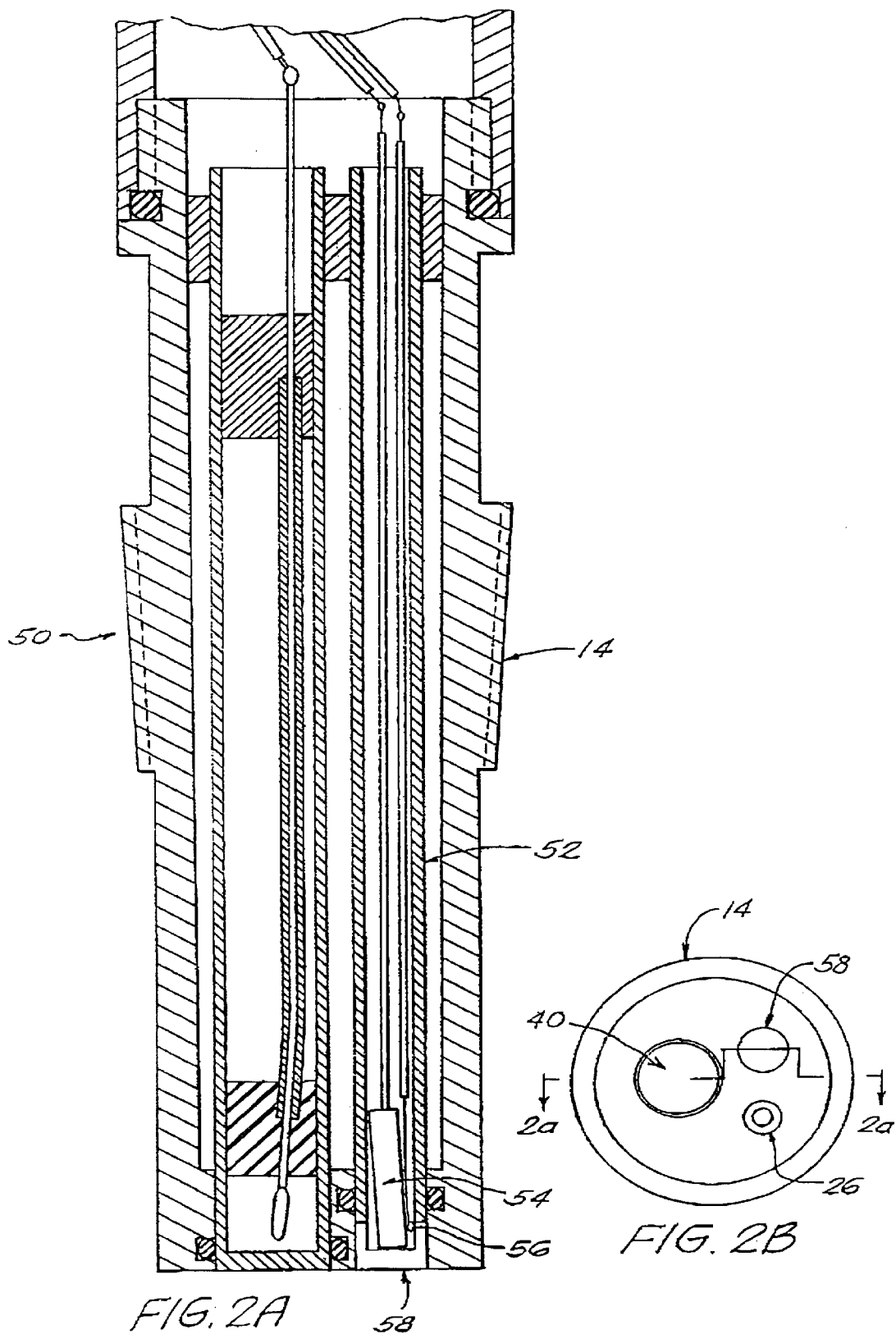

SENSOR FOR ELECTROMETRIC MEASUREMENT

BACKGROUND OF THE INVENTION

The present invention relates to a sensor having a reference electrode, more specifically, a reference electrode with an internal reference junction. Reference electrodes are commonly used in connection with ion-selective electrodes to determine the concentration of ions in solution. For example, a reference electrode is often used with an electrochemical ion-measuring electrode, such as a glass pH electrode, to measure the concentration of hydrogen ions in a process solution. In particular, the present invention relates to sensors for measuring the ion concentration of a process solution, e.g., fluids, slurries, and the like.

The basis of the electrometric measurement of pH is the development of a potential gradient across a membrane of specific composition, when interposed between solutions having different concentrations of hydrogen ion. The potential developed across the membrane is quantitatively related to the concentration gradient of hydrogen ion and can be applied to a known measuring circuit to measure the pH of the sample. Because the potential developed across the glass is to be measured, electrolytic contacts must be made to the solutions on either side of the membrane. The potentials generated by these contacts are controlled using, for example, Ag/AgCl reference electrodes with controlled concentrations of potassium chloride (KCl) solution.

The conventional, external reference electrode has two components that contribute to the total potential measured across the cell: a thermodynamic potential and a liquid junction potential. The thermodynamic potential is derived from the electrochemical half-cell, whereas the liquid junction potential is derived from the difference in the ionic composition of the internal salt bridge electrolyte and the process solution being measured. For example, where the reference electrode half-cell reaction is:

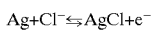

the potential generated may be fixed by: (1) controlling the concentration of chloride ion, i.e. Cl⁻, at a constant value; and (2) preventing interfering ions in the process solution from approaching the reference half-cell. In prior reference electrodes, these conditions are typically achieved by filling the reference electrode with potassium chloride (KCl), often within an internal chamber, which is connected to a salt bridge using an internal ceramic barrier. In such electrodes, electrolytic contact between the salt bridge and the process solution is made via an external ceramic barrier, and the salt bridge is stationary, i.e. non-flowing. In this configuration, both the liquid junction and the half-cell potential may be compromised during ingress of the process solution into the internal salt-bridge and reference half-cell solutions. Thus, accurate measurements require that cell voltage varies only with the concentration of the ion of interest, and that the reference electrode potential remain constant, i.e. unaffected by the composition of the process solution. In fact, it is known that the reference electrode is often the cause of poor results obtained from measurements with ion-selective electrodes. See Brezinski, D. P., *Analytica Chimica Acta*, 134 (1982) 247–62, the contents of which are hereby incorporated by reference.

In addition, the development of process sensors has tended toward probes with smaller diameters. This trend has made the construction of highly accurate and stable sensors more difficult. For example, in certain sensor designs, positioning the reference electrode further away from the process solution has resulted in decreased accuracy, due to decreased thermal accuracy. Thus, it would be desirable to have a sensor with increased stability and accuracy of measurement which decreases or eliminates the ingress of process solution. There is also a need for improved sensors having smaller diameters while also minimizing the process-wetted portion of the sensor.

In view of these considerations, it is an object of this invention to provide a reference electrode that minimizes or prevents back-flow of contaminants or materials from the process solution through the external junction. It is also an object of this invention to provide a durable, economical and versatile reference electrode that is easy to fabricate, use, install, calibrate and maintain. These and other objects are satisfied by the invention described herein.

SUMMARY OF THE INVENTION

The present invention provides a sensor with a reference electrode and a flowing electrolyte. The invention provides sensors that operate with relatively high accuracy and stability by minimizing or eliminating ingress of contaminants from a process solution through the external junction of the sensor. In one aspect, the invention includes a sensor having a pressurized reservoir which provides flow of an electrolyte. In another aspect, the invention provides a sensor having a non-metallic solution ground. In yet another aspect, the invention includes a resistance temperature device bonded to a non-metallic solution ground.

In one embodiment, the invention provides a sensor having a reference electrode, a flowing electrolyte in electrolytic contact with the reference electrode, a pressurized reservoir for providing flow of the electrolyte, a reference junction and an external junction in electrolytic contact with the reference electrode and wherein the electrolyte flows between the junctions.

In another embodiment, the invention provides a sensor having a reference electrode, a flowing electrolyte in electrolytic contact with the reference electrode, a pressurized reservoir for providing flow of the electrolyte, and a non-metallic ground disposed at a sensing surface.

In yet another embodiment, the invention provides a sensor having a reference electrode, a flowing electrolyte in electrolytic contact with the reference electrode, a pressurized reservoir for providing flow of the electrolyte, a non-metallic ground disposed at a sensing surface, and a resistance temperature device bonded to the non-metallic ground.

Sensors of the invention may be used to measure various parameters of a fluid, e.g., ion concentration. In one preferred embodiment, the sensor is a pH sensor, i.e. a sensor to measure hydrogen ion concentration, having a reference electrode, a flowing electrolyte in electrolytic contact with the reference electrode, a pressurized reservoir for providing flow of the electrolyte, a reference junction, and an external junction in electrolytic contact with the reference electrode. The electrolyte flows from the pressurized reservoir to the external junction. In another preferred embodiment, the pH electrode includes a non-metallic ground disposed at a sensing surface. In yet another preferred embodiment, the pH sensor includes a resistance temperature device bonded to the non-metallic ground. In a particularly preferred embodiment, the non-metallic ground extends beyond the end of the lower housing and, even more preferably, the non-metallic ground is substantially conical in shape.

In still another embodiment, the invention provides a method of manufacturing a sensor having a resistance temperature device and a non-metallic ground, the method including the steps of melting the non-metallic ground in contact with the resistance temperature device and allowing the non-metallic ground to solidify in contact with the resistance temperature device, thus ensuring optimal thermal contact. In yet another embodiment, the invention includes a method of manufacturing a sensor having a resistance temperature device and a non-metallic ground that is substantially conical in shape.

BRIEF DESCRIPTION OF THE DRAWINGS

FIG. 1a is a cross-section of one embodiment of a sensor according to the present invention, taken along section line 1a–1a of FIG. 1b.

FIG. 1b is an end view of the embodiment depicted in FIG. 1a and depicts the sensing surface of the sensor.

FIG. 2a is a cross-section of another embodiment of a sensor according to the present invention, taken along section line 2a–2a of FIG. 2b, and showing aspects of the resistance temperature device and the solution ground.

FIG. 2b is an end view of the embodiment depicted in FIG. 2a and depicts the sensing surface of the sensor.

DETAILED DESCRIPTION OF THE ILLUSTRATED EMBODIMENTS

Figure 3A:
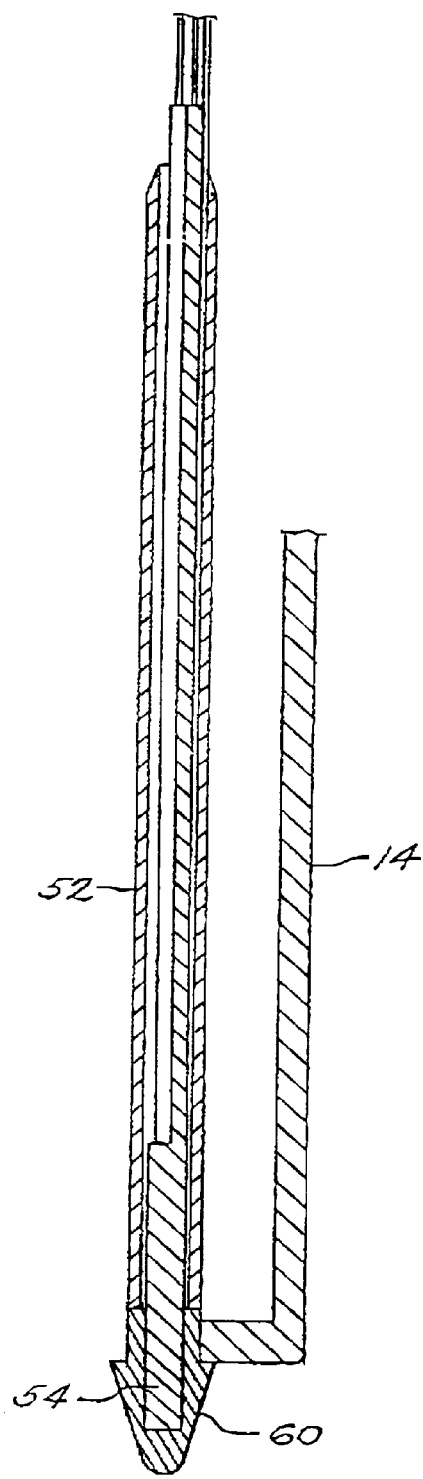
FIG. 3a is a cross-section of one embodiment of a sensor according to the present invention and depicts a solution ground that is substantially conical in shape.

One aspect of this invention provides a sensor having a reference electrode for use with electrochemical ion measuring electrodes, e.g. pH electrodes. The sensor has a flowing electrolyte that provides electrolytic contact between the internal reference half-cell and the process wetted junction. This flow of electrolyte prevents back flow of contaminants or other materials from the process solution through the external junction and into the electrolyte, thereby minimizing unwanted liquid junction potentials in the external junction. Further, this arrangement reduces the likelihood of reference half-cell contamination. A sensor in accord with the invention can be manufactured with a relatively small diameter of, e.g. 0.75 in (1.9 cm). In addition, sensors of the invention may be designed to reduce the length of the process wetted portion, for example, to about 0.5 in (1.3 cm).

A sensor 10 according to one embodiment of this invention has, as shown in FIGS. 1a and 1b, an upper housing 12 and a lower housing 14, and includes a pressurized reservoir 20 for electrolyte 22 which is acted upon by a piston 18. The illustrated embodiment includes a spring 16 acting on the piston 18, to create positive flow of electrolyte 22. A porous member 24 is provided between the reservoir 20 and the external junction 26. Preferably, the porous member 24 is made of glass material. Reference electrode 34 is encased by internal junction 32, which is a cation exchange membrane. Preferably, the cation exchange membrane is a sulphonated polytetrafluoroethylene membrane, such as that commercially available from DuPont under the trade name NAFION®. Membrane 40 surrounds measuring electrode 38, which is operatively connected to reference electrode 34.

FIGS. 2a and 2b show another sensor 50 according to the invention, which includes a resistance temperature device 54. As further shown in the illustrated embodiment, ground wire 56 is operatively connected to solution ground 58. In a preferred embodiment, solution ground 58 is made of a non-metallic material. Most preferably, the solution ground 58 is made of a conductive polymer, such as conductive polyvinyldifluoride, sold by Elf Atochem, N.A. under the trade name KYNAR®. Preferably, the solution ground 58 is bonded to insulating ground tube 52.

Figure 3B:
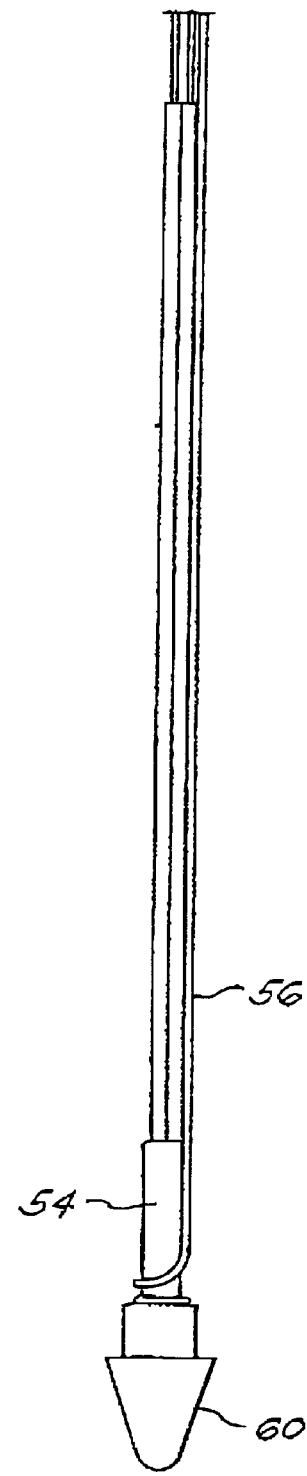
FIG. 3b is a view of the embodiment depicted in FIG. 3a showing aspects of the resistance temperature device and a solution ground that is substantially conical in shape.

FIGS. 3a and 3b show another sensor according to the invention, which includes a substantially conical non-metallic ground 60. As further shown in the illustrated embodiment, the substantially conical non-metallic ground 60 extends beyond the end of lower housing 14. The resistance temperature device 54 extends into the substantially conical non-metallic ground 60, which is bonded to ground tube 52. FIG. 3b illustrates ground wire 56 in operative connection with the resistance temperature device 54.

In one embodiment, the invention provides a sensor 10 with a pressurized reservoir 20 for creating and controlling flow of an electrolyte 22. The reservoir 20 may be pressurized in a variety of ways. For example, pressure may be imparted by a piston 18 which subjects the electrolyte 22 to a controlled pressure. In a preferred embodiment, the piston 18 is a spring actuated piston. Other fluid motive means known in the art may be used in accordance with the invention. For example, an external pressure source may be used to impart flow of the electrolyte, e.g., a pump may be used to pump electrolyte through a capillary. In a preferred embodiment, the fluid motive means is a mechanism which creates a pressure drop across a porous member 24. In another preferred embodiment, the flow rate of electrolyte 22 is limited to less than about 20 $\mu$L/day. Preferably, the pressure exerted on the electrolyte 22 is approximately 200 psig.

In another embodiment, the invention provides a sensor 50 having a non-metallic ground 58 positioned to contact a process solution. The ground 58 is disposed at a sensing surface of the sensor, i.e. any surface which is in contact with the process solution. In a preferred embodiment, the non-metallic ground 58 is an electrically conductive polymer. In a most preferred embodiment, the non-metallic ground 58 is made of polyvinyldifluoride, such as that commercially available from Elf Atochem, N.A. under the trade name KYNAR®. In a preferred embodiment, a non-metallic ground of electrically conductive polymer is bonded to a non-conductive polymer tube 52, thus ensuring optimal thermal contact.

In one particularly preferred embodiment, the invention provides a sensor having a resistance temperature device 54 that is bonded to a non-metallic ground 58. The invention also provides a method of manufacturing a sensor 50 having a resistance temperature device 54 bonded to a non-metallic ground 58. The method includes the steps of melting the non-metallic ground 58 in contact with the temperature device 54 and allowing the non-metallic ground 58 to solidify in contact with the device 54. The geometrical shape of the non-metallic ground 58 is not particularly limited, however, in a preferred embodiment, the non-metallic ground extends beyond the end of the lower housing 14 and is substantially conical in shape.

In yet another preferred embodiment, the invention provides an internal (reference) junction 32 which includes a cation exchange membrane. Most preferably, the membrane is a sulphonated polytetrafluoroethylene membrane, such as that commercially available from DuPont under the trade name NAFION®. A cation exchange membrane, i.e. a membrane that is permeable to many cations and polar molecules, is preferred as a material for a reference junction due to its ability to pass charge as positively charged cations. The cation exchange membrane is likewise substantially impermeable to anions and non-polar species.

In one preferred embodiment, a cation exchange membrane encases the reference electrode 34. Encasing the reference electrode 34 in a cation exchange membrane serves to maintain the Chloride level and minimize effects of contamination from external sources. It also maintains the Ag+ level due to the fact that Ag+ forms a negatively charged complex of the form $Ag(Cl_n)^{-(n-1)}$. This also inhibits the AgCl from reaching the external junction 26, where decreased KCl levels due to diffusion of the external process may result in the precipitation of AgCl. Such precipitation may cause clogging of the junction and a resulting noisy liquid junction potential.

For a sensor 10 which uses AgCl-saturated, 1 M KCl electrolyte solution 22, the cation exchange membrane may be prepared by immersion in a solution of 1 M KCl. This process creates an electrical junction across the membrane, wherein potassium ions associate with the membrane. In operation, when a charge is drawn from an attached measuring device, potassium ions from the internal solution associate with the membrane, causing potassium ions to dissociate from the other side of the membrane. In contrast, conventional porous ceramic junctions require negative ion movement in the opposite direction in order to maintain charge balance. Thus, while the flowing electrolyte 22 minimizes back diffusion of contaminants through the external junction 26, even if contaminants were to reach this membrane, there would be little effect on the reference potential until the concentration builds to an appreciable fraction of the relatively high cation (e.g., $K^+$) concentration.

According to the present invention, flow of electrolyte 22 may be controlled, in part, by a porous member 24 positioned between a pressurized reservoir 20 and an external junction 26. Preferably, electrolyte flow may be controlled to a flow rate in the range 0.1 to 20 $\mu L$/day by creating a pressure differential across a microporous VYCOR® glass (Corning Glass code 7930). See T. H. Elmer, "Porous and Reconstructed Glasses," Engineered Materials Handbook, Vol. 4: Ceramics and Glasses, which is hereby incorporated by reference. The particularly useful property of VYCOR® in this embodiment is the very narrow pore size distribution exhibited by this material. This renders flow rates very predictable and constant. The reference electrode 34 is located downstream from this porous member 24 and is isolated from the process by an external liquid junction. As discussed herein, the external junction 26 is preferably a relatively low porosity alumina ceramic. Based on a maximum internal fluid capacity of 8 mL and a useful life of 1-year, the maximum permissible flow rate should average no greater than about 20 $\mu L$/day.

In a preferred embodiment, the internally pressurized design of the invention provides an outward flow of electrolyte 22 with a flow rate sufficient to overcome inward diffusion of process through the external junction 26. The effectiveness of an approximately 1 $\mu L$/hr flow rate to prevent inward diffusion was demonstrated experimentally. A multiple syringe pump capable of accurately delivering controlled flows in the range 0.5 to 2.0 $\mu L$/hr was connected into flow cells containing M/871CR conductivity cells. The cells were connected to 870ITCR transmitters and a data logger to monitor conductivities in the range 0 to 100 $\mu S$/cm. The diffusion barrier ceramic was placed at the output of the flow cell at a position up-stream and in close proximity to the conductivity sensor. At the start of each experiment, the system, syringe, flow cell and external tube containing diffusion barrier were filled with deionized, deaerated water and the assemblies were placed in a thermostated bath to eliminate thermal expansion effects on the flow-rates. To ensure against leaks (this minuscule flow-rate is virtually impossible to detect visually), the output flow was monitored using 1/32" id capillary tubing (volumetric displacement, 12.5 $\mu L$/inch). In each case the system was allowed to operate for several days to establish a baseline of conductivity with time; i.e. to ensure no conductivity change due to inwards leaks from the temperature bath or from corrosion within the flow cells. To start the salt test, the exit capillary on external tube was carefully withdrawn using a syringe and replaced with 1 M KCl. The flow measuring tube was purged of liquid and then reinstalled. No increase of conductivity at this point signified outflow and, thus, prevention of diffusion in.

The electrical resistance of three samples of Ceramtek 244B type ceramics were tested for electrical resistance and the results are shown in Table I. The standard procedure measures the iR drop created by a polarizing current of 0.2 $\mu A$ across the ceramic immersed in 1 M KCl using two NAFION encased Ag, AgCl/1.0 M KCl reference assemblies a non-polarizable electrolytic contacts.

TABLE I

|  | V1[a] (mV) | V2[b] (mV) | R, Kohm[c] | R, Kohm[corr.] |
|---|---|---|---|---|
| NAFION/NAFION | 0.20 | 0.36 | 0.80 | N/A |
| Sample 1 | 0.89 | 3.60 | 13.55 | 12.75 |
| Sample 2 | 1.07 | 4.61 | 17.7 | 16.90 |
| Sample 3 | 0.66 | 4.33 | 18.35 | 17.55 |

NAFION/NAFION represents the resistance of the two NAFION assemblies without the junction between them and is essentially the combined resistance of the two NAFION barriers.
[a]Measured voltage without applied current
[b]Measured voltage with 0.2 $\mu A$ applied
[c]R, Kohm = $\{(V_2 - V_1)/(2E - 6)\} \cdot 10^{-3}$, where the V's are expressed in mV Kohm[corr] represents ceramic after subtracting 0.80K from NAFION/NAFION:

Although the external junction 26 is not typically used to control flow rate in normal operation, it presents a significant restriction to diffusion with minimum electrical impedance. Experiments were conducted to establish an empirical relationship between volumetric flow rate and ceramic junction electrical resistance. Preferably, flow is minimized and electrical resistance across the ceramic is limited to less than 20 kohms. Reference conditions for flow rate measurements were determined by mounting the ceramics in glass tubes to ensure flow through, rather than around, the ceramic. Ceramics were mounted in Corning Type 0120 glass (potash soda lead) and deionized water, pressurized with 10 psig air provided the flow. Flow was measured as the linear displacement of the air/water interface along a tube having an id of 1/32. (12.5 $\mu L$/in). Data for two ceramic materials are shown in Table II.

TABLE II

Flow Rates and Electrical Resistance of External Diffusion Barriers
Ceram-tek 244B, 0.053" diam x 0.150" long
Average Flow Rate ($\mu$L/hr)

| Sample | Flow Rate |
|---|---|
| Sample 1 | 22.6 |
| Sample 2 | 24.4 |
| Sample 3 | 24.2 |

Average Resistance, three samples, 15.7 K

A variety of reference electrodes and electrolytes are known and may be used with sensors of the invention. An ordinarily skilled artisan can select an electrode/electrolyte combination for a particular application without undue experimentation. In a particularly preferred embodiment, the invention provides a pH sensor. The Ag/AgCl, 1 M KCl, Sat AgCl reference electrode used in the pH sensor is isolated from the process by an external junction and an internal reference junction which includes a NAFION® membrane barrier. A positive outflow of electrolyte counteracts inward diffusion of process and additionally inhibits clogging of the external junction by the process solution. If desired, diffusional transport of process solution to the reference junction is further restricted by a relatively long path length between the external and reference junctions.

Preferably, the reference electrode 34 of the present invention produces and maintains a constant (i.e., non-polarizable) electromotive potential that is unaffected by the small electrical current requirement of the measuring device to which it is connected. Further, the reference electrode preferably maintains its stability over the entire temperature and pressure range requested and must be protected from exposure to the various chemical species in the large variety of processes in which these sensors are applied.

Silver, silver chloride, in contact with a fixed concentration of KCl, is preferred for a pH sensor. When properly constructed, its potential is non-polarizable at the current densities employed and its temperature dependence closely obeys theoretical predictions. At equilibrium, the following electrochemical reaction fixes the electrode potential:

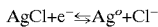

$$AgCl + e^- \rightleftharpoons Ag^\circ + Cl^-$$

Silver chloride, plated on a silver wire, provides the reference terminal. When current is drawn through the cell, this reaction can proceed either to the right or left depending on current direction. The potential will remain constant as long as 1) sufficient AgCl remains on wire, 2) the chloride concentration remains constant and 3) extraneous ionic species do not approach the proximity of the electrode and compete with the chloride ion.

Silver chloride solubility is related to concentration of KCl used in the salt bridge. The solubility of AgCl in 0, 1, 2, 3, and 4 M KCl is 0.01, 0.1, 0.6 2.2, and 8.0 mM, respectively. The increase in solubility is due to formation of negatively charged complex ions having the general formula $Ag(Cl_n)^{-(n-1)}$. Use of electrolyte 22 having high concentration of KCl is desirable for limiting electrical resistance over the path that isolates the internal reference junction 32 physically from the process. Also, the ability of KCl to form relatively clean junctions with the process samples with relatively small electrical junction potentials is desirable. However, when the concentration of KCl is diluted in the porous junction, AgCl precipitates and clogs it, causing spurious and erratic liquid junction potentials. Thus, a 1 M KCl solution is preferable because, at this concentration, the solubility of AgCl is roughly 1% of that in 4 M KCl. This concentration of electrolyte should be used throughout the probe; in the glass electrode internal reference electrode (here adjusted to pH 7), in the working reference electrode and in the electrolyte 22. In this way, the isopotential point for the system is established at pH 7.

If desired, the electrolyte used may contain a glycol to provide freeze protection. For example, the electrolyte used may be 0.33 M KCl with 40 vol. % ethylene glycol, or 1 M KCl with 25% propylene glycol. NAFION® membrane resistance may vary significantly with degree of hydration and it is therefore necessary to condition the membrane in the electrolyte. This is done by heating the NAFION membrane in the electrolyte for one hour at 95–100° C. The membrane is then stored in a closed container of this electrolyte until used.

In a pH sensor according to the invention, the pH function of the glass membrane depends on its bulk composition. It presents a stable ionic exchange equilibrium with hydrogen ions in contact with the internal and external surfaces. Electrolytic transport of cations (usually $Na^+$ or $Li^+$) provide sufficient conductivity across the membrane to allow measurement of this potential by the connected analyzer with sufficiently high input impedance. Silicate ($SiO_2$) forms the stable and durable anionic framework in glass that provides ion exchange sites necessary for the pH function. Preferable pH glass formulations contain at least 50% $SiO_2$. This property governs the ultimate temperature limits and chemical compatibility properties of pH glass membranes. Alkali metal ions such as $Li^+$, $Na^+$ and $Cs^+$ provide the mobile charge carriers that impart electrolytic conductivity to these glasses.

Formulations with $Na^+$ provide high conductivity, hence low resistance glasses, but the presence of $Na_2O$ may lead to high measurement errors in solutions of high pH (the so-called sodium ion error) and also to increased solubility (corrosion) of the glass at elevated temperatures. Because of the relatively low bulk resistivity of this glass it is possible to fabricate this membrane in a "flat-glass" design for use in applications where protrusion of a fragile element into the process is objectionable. This membrane demonstrates ideal Nernstian response over the 2–12 pH range and 0–85° C. temperature range.

Lithia glasses ($Li_2O$) have significantly less measurement error at high pH than soda glasses and significantly increased corrosion resistance at elevated temperature. The tradeoff is that Li+ is significantly less mobile in the glass yielding higher bulk resistivity. The high resistivity requires that the membranes be thinner and have larger area than would be practical with a flat-glass design. Thus, a spherical domed bulb design is preferable for high temperature wide pH range measurements.

The geometric shape of the non-metallic ground in a sensor of the present invention is not particularly limited. The nonmetallic ground may be either machined or made by injection molding according to procedures known in the art. In a preferred embodiment, the non-metallic ground extends beyond the end of the sensor housing or body and into the process solution. More preferably, the geometric shape of such a ground is selected to provide a relatively large surface area exposed to the process solution. Additionally, it is preferable to use a non-metallic ground having relatively thin walls. This combination of relatively large surface area and relatively thin walls serves to minimize the response time of the resistance temperature device (RTD), and also to minimize the possibility of entrapment of any solids present in the process solution.

To demonstrate one of the advantages of the present invention, a sensor according to the invention was compared to certain commercially available sensors. Specifically, the speed of thermal response of a probe of the invention was compared with the speeds of thermal response for various commercially available pH probes. Briefly, for each probe, the speed of thermal response was measured by first determining the resistance of the RTD in the probe at ambient room temperature. Each probe was then placed in boiling water. The RTD resistance was then measured every 10 to 20 seconds, depending on the rate of response. The response time was defined as the time a give probe takes to read 90% of the change from ambient temperature to boiling water.

Figure 4:
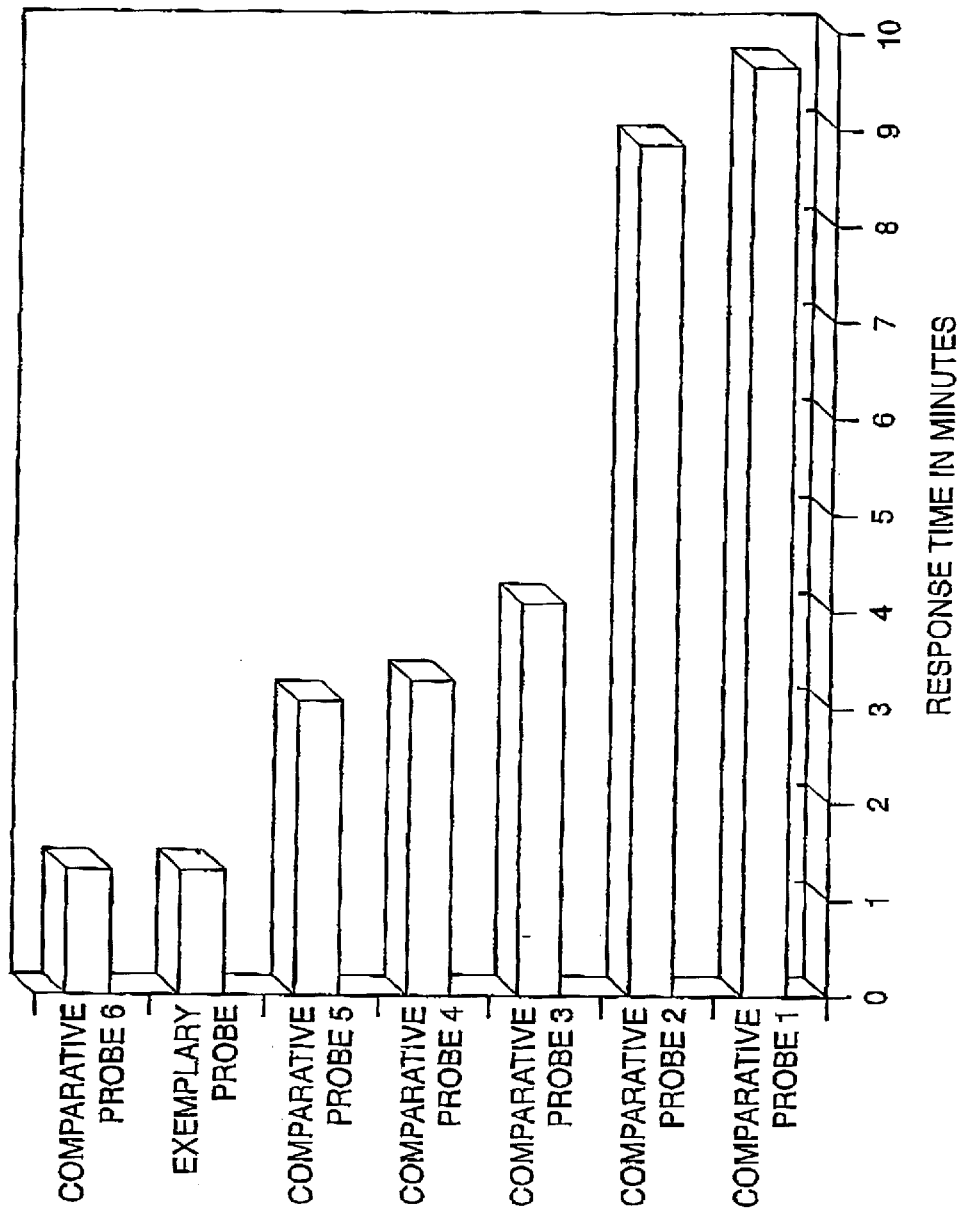
FIG. 4 is a graph comparing the response time of the temperature resistance device of a sensor of the invention with the response time of some commercially available sensors.

FIG. 4 and Table III show a comparison of the response times of a sensor according to the invention with that of various probes. The Exemplary Probe used in the experiment was a sensor according to the invention having a non-metallic solution ground extending beyond the end of the sensor housing and having a substantially conical shape. Comparative Probes 1–6 are commercially available pH probes. In particular, Comparative Probe 1 is a TBI Model 557, Comparative Probe 2 is a TBI Model 551, Comparative Probe 3 is a Mettler Inpro 4500, Comparative Probe 4 is a Iontron Ultra 10, Comparative Probe 5 is a Rosemount TupH, and Comparative Probe 6 is an ASI Model 68 Versaprobe. Each of Comparative Probes 1 through 5 is a plastic-bodied pH probe with the RTD positioned away from the process solution interface. Comparative Probe 6 uses a glass/metal interface with the RTD to achieve its response time. It is clear from the data presented in FIG. 4 and Table III that the sensor of the present invention provides dramatically increased response time as compared to conventional probes and, in fact, is capable of thermal response times that previously attainable only with a metallic interface.

TABLE III

Comparison of Thermal Response Times for Various Probes

| Probe | Manufacturer/Model | Response Time (Min.) |
| --- | --- | --- |
| Comparative Probe 1 | TBI Model 557 | 9.6 |
| Comparative Probe 2 | TBI Model 551 | 8.8 |
| Comparative Probe 3 | Mettler Inpro 4500 | 4.0 |
| Comparative Probe 4 | Iontron Ultra 10 | 3.2 |
| Comparative Probe 5 | Rosemount TupH | 3.0 |
| Comparative Probe 6 | ASI Model 68 Versaprobe | 1.2 |
| Exemplary Probe | Foxboro COP. | 1.2 |

The invention also provides a method of manufacturing a sensor having a resistance temperature device (RTD) 54 and a non-metallic ground 58. An RTD/ground assembly was prepared as follows. A wire lead was wrapped around the body of an RTD to form a subassembly. This subassembly was then inserted into a piece of electrically conductive polymer (KYNAR®), using a slip/press fit. An insulating polymer piece was then placed over the subassembly. The inner diameter of the insulating polymer preferably provides a tight fit over the wire lead. The resulting assembly was placed in a metal heating block to melt the two polymer pieces to the RTD and wire. The process resulted in: (1) a hermetic seal between the polymer pieces; (2) an intimate electrical connection between the lead wire and the assembly; (3) a mechanical bond between the RTD and the assembly; and (4) an intimate thermal contact between the RTD and the non-metallic solution ground.

INCORPORATION BY REFERENCE

All patents, published patent applications and other references disclosed herein are hereby expressly incorporated herein in their entireties by reference.

EQUIVALENTS

Those skilled in the art will recognize, or will be able to ascertain using no more than routine experimentation, that the apparatus and embodiments described above may be modified without departing from the broad inventive concept described herein. Thus, the invention is not to be limited to the particular embodiments disclosed herein, but is intended to cover modifications within the spirit and scope of the present invention as defined by the appended claims.

We claim:

1. A sensor of a fluid parameter, the sensor comprising
   a reference electrode,
   an electrolyte in electrolytic contact with the reference electrode,
   a pressurized reservoir,
   a reference junction,
   an external junction, and,
   a porous member to control a flow of the electrolyte from the reservoir to minimize inward diffusion through the external junction.

2. The sensor of claim 1 further comprising a piston for subjecting the electrolyte to a controlled pressure.

3. The sensor of claim 2 wherein the piston is a spring actuated piston.

4. The sensor of claim 1 wherein the porous member is positioned between the reservoir and the external junction.

5. The sensor of claim 1 wherein the porous member is a glass material.

6. The sensor of claim 1 wherein the reference junction comprises a cation exchange member.

7. The sensor of claim 6 wherein the member is a sulphonated polyfluoroethylene membrane.

8. The sensor of claim 1 wherein the external junction is made of a ceramic material.

9. The sensor of claim 1 further comprising an external pressure source for subjecting said electrolyte to a controlled pressure.

10. The sensor of claim 1 further comprising a non-metallic ground disposed at a sensing surface.

11. The sensor of claim 10 further comprising a housing wherein the non-metallic ground extends beyond an end of the housing.

12. The sensor of claim 11 wherein the non-metallic ground is substantially conical.

13. A sensor comprising
    an external junction,
    a reference electrode,
    an electrolyte in electrolytic contact with the reference electrode and the external junction,
    a pressurized reservoir,
    a porous member to control a flow of the electrolyte from the reservoir to minimize inward diffusion through the external junction, and
    a non-metallic ground disposed at a sensing surface.

14. The sensor of claim 13 wherein the non-metallic ground comprises a conductive polymer.

15. The sensor of claim 14 wherein the polymer is polyvinyldiflourine.

16. The sensor of claim 13 further comprising a piston in communication with the electrolyte for subjecting the electrolyte to a controlled pressure.

17. The sensor of claim 16 wherein the piston is a spring actuated piston.

18. The sensor of claim 13 wherein the porous member is positioned between the reservoir and the external junction.

19. The sensor of claim 18 wherein the porous member is made of glass material.

20. The sensor of claim 13 wherein the sensor comprises a reference junction.

21. The sensor of claim 20 wherein the reference junction comprises a cation exchange membrane.

22. The sensor of claim 21 wherein the membrane is a sulphonated polyfluoroethylene membrane.

23. The sensor of claim 13 further comprising an external pressure source for subjecting said electrolyte to a controlled pressure.

24. The sensor of claim 13 further comprising a housing wherein the non-metallic ground extends beyond an end of the housing.

25. The sensor of claim 24 wherein the non-metallic ground is substantially conical.

26. A sensor comprising
a reference electrode,
an electrolyte in electrolytic contact with the reference electrode,
a pressurized reservoir,
a porous member to control a flow of the electrolyte from the reservoir to minimize inward diffusion through the external junction,
a non-metallic ground disposed at a sensing surface, and
a resistance temperature device bonded to the non-metallic ground.

27. The sensor of claim 26 wherein the non-metallic ground comprises a conductive polymer.

28. The sensor of claim 27 wherein the polymer is polyvinyldifluorine.

29. The sensor of claim 26 further comprising a piston in communication with the electrolyte for subjecting the electrolyte to a controlled pressure.

30. The sensor of claim 29 wherein the piston is a spring actuated piston.

31. The sensor of claim 26 wherein the porous member is positioned between the reservoir and an external junction.

32. The sensor of claim 31 wherein the porous member is made of glass material.

33. The sensor of claim 26, further comprising a reference junction wherein the reference junction comprises a cation exchange membrane.

34. The sensor of claim 33 wherein the membrane is a sulphonated polyfluoroethylene membrane.

35. The sensor of claim 26 further comprising an external pressure source for subjecting said electrolyte to a controlled pressure.

36. The sensor of claim 26 further comprising a housing wherein the non-metallic ground extends beyond an end of the housing.

37. The sensor of claim 26 wherein the non-metallic ground is substantially conical.

38. A pH sensor having a housing and comprising
a reference electrode mounted in the housing,
a measuring electrode mounted in the housing and operatively connected to the reference electrode,
a fluid conduit for containing an electrolyte in electrolytic contact with the reference electrode,
a pressurized reservoir in fluid communication with the fluid conduit,
a reference junction encasing the reference electrode,
an external junction in electrolytic contact with the reference electrode, and,
a porous member to control a flow of the electrolyte from the pressurized reservoir to minimize inward diffusion through the external junction.

39. The pH sensor of claim 38 further comprising a non-metallic ground disposed at a sensing surface.

40. The pH sensor of claim 39 further comprising a housing wherein the non-metallic ground extends beyond an end of the housing.

41. The pH sensor of claim 40 wherein the non-metallic ground is substantially conical.

42. The pH sensor of claim 41 wherein the piston is a spring actuated piston.

43. The pH sensor of claim 39 wherein the non-metallic ground comprises a conductive polymer.

44. The pH sensor of claim 43 wherein the polymer is polyvinyldifluorine.

45. The pH sensor of claim 44 further comprising a piston in communication with the electrolyte for subjecting the electrolyte to a controlled pressure.

46. The pH sensor of claim 38 wherein the porous member is positioned between the reservoir and an external junction.

47. The pH sensor of claim 46 wherein the porous member is made of glass material.

48. The pH sensor of claim 38 wherein the reference junction comprises a cation exchange membrane.

49. The pH sensor of claim 48 wherein the membrane is a sulphonated polyfluoroethylene membrane.

50. The pH sensor of claim 38 further comprising an external pressure source for subjecting said electrolyte to a controlled pressure.

51. The pH sensor of claim 38 wherein the electrolyte is a solution of AgCl-saturated KCl.

52. The pH sensor of claim 38 wherein the reference electrode is made of silver-silver-chloride.

53. A sensor having a housing and comprising
a reference electrode mounted in the housing,
an electrolyte in electrolytic contact with the reference electrode,
an external junction,
a pressurized reservoir,
a porous member for controlling a flow of the electrolyte from the pressurized reservoir to minimize inward diffusion through the external junction, and
a non-metallic ground disposed at a sensing surface.

54. The sensor of claim 53 wherein the non-metallic ground extends beyond an end of the housing.

55. The sensor of claim 53 wherein the non-metallic ground is substantially conical.

56. The sensor of claim 53 further comprising a reference junction positioned between the electrolyte and the reference electrode.

57. The sensor of claim 56 wherein the reference junction comprises a cation exchange membrane.

58. The sensor of claim 57 wherein the membrane is a sulphonated polyfluoroethylene membrane.

59. The sensor of claim 53 further comprising an external junction in electrolytic contact with the reference electrode.

60. The sensor of claim 59 wherein the external junction is made of ceramic material.

61. The sensor of claim 53 wherein the fluid motive means comprises a piston in communication with the electrolyte for subjecting the electrolyte to a controlled pressure.

62. The sensor of claim 61 wherein the piston is a spring actuated piston.

63. The sensor of claim 53 wherein the porous member is made of glass material.

64. The sensor of claim 53 further comprising an external pressure source for subjecting the electrolyte to a controlled pressure.

65. The sensor of claim 53 wherein the non-metallic ground comprises a conductive polymer.

66. The sensor of claim 65 wherein the polymer is polyvinyldifluorine.

67. The sensor of claim 53 further comprising a resistance temperature device bonded to the non-metallic ground.

68. The sensor of claim 53 further comprising a measuring electrode operatively connected to the reference electrode.

69. The sensor of claim 53 wherein the electrolyte is a solution of AgCl-saturated KCl.

70. The sensor of claim 53 wherein the reference electrode is made of silver-silver chloride.

* * * * *